United States Patent [19]
Tegeder

[11] Patent Number: 5,632,085
[45] Date of Patent: May 27, 1997

[54] METHOD FOR MAKING AN ELECTRICAL CONTACT FOR A VITREOUS CARBON ELECTRODE

[75] Inventor: Volker Tegeder, Erlangen, Germany

[73] Assignee: Pacesetter AB, Solna, Sweden

[21] Appl. No.: 554,769

[22] Filed: Nov. 7, 1995

[30] Foreign Application Priority Data

Nov. 9, 1994 [DE] Germany .................. 44 40 001.2

[51] Int. Cl.$^6$ .................................................. H01R 43/20
[52] U.S. Cl. .................... 29/876; 156/86; 264/29.1; 607/116
[58] Field of Search .................... 29/619, 621, 854, 29/842, 844, 447; 156/86, 89, 293; 264/29.1; 607/116, 119

[56] References Cited

U.S. PATENT DOCUMENTS

| | | |
|---|---|---|
| 1,181,811 | 5/1916 | Wallace . |
| 3,722,005 | 3/1973 | Cowland ..................... 128/2 |
| 4,609,508 | 9/1986 | Edeling et al. . |
| 4,773,433 | 9/1988 | Richter et al. . |
| 4,917,760 | 4/1990 | Richter et al. ................ 156/655 |

FOREIGN PATENT DOCUMENTS

| | | |
|---|---|---|
| 0 140 127 | 5/1985 | European Pat. Off. . |
| 0 173 860 | 3/1986 | European Pat. Off. . |

Primary Examiner—P. W. Echols
Assistant Examiner—Adrian L. Coley
Attorney, Agent, or Firm—Hill, Steadman & Simpson

[57] ABSTRACT

A method for making an electrical contact for a vitreous carbon electrodes includes the steps of making a bore in an electrode blank of a cross-linked artificial resin forming the electrode blank into an electrode body. A solid or hollow pin, or a sleeve, composed of a biocompatible, refractory metal is introduced into the bore. If a pin is to be used, the bore is made to extend only partially into the electrode body, if a sleeve is used the bore extends completely through the body. The pin or sleeve has smaller dimensions than the bore; if a pin is used it projects from one side of the electrode body and if a sleeve is used it projects from both sides of the electrode body. The electrode blank is subjected to a pyrolysis, whereby the cross-linked artificial resin is converted into vitreous carbon and the electrode body shrinks onto the pin or sleeve.

15 Claims, No Drawings

METHOD FOR MAKING AN ELECTRICAL CONTACT FOR A VITREOUS CARBON ELECTRODE

BACKGROUND OF THE INVENTION

1. Field of the Invention

The present invention is directed to a method for making an electrical contact for a vitreous carbon electrode for subsequent connection to an electrical conductor.

1. Description of the Prior Art

Electrodes of vitreous carbon are suitable as implantable actuators and sensors in biomedicine (see German PS 26 13 072) Vitreous carbon electrodes have good biocompatibility and can have a high capacitance, and the cost for materials is low compared to other electrode materials. As used herein, the terms actuator or effector mean electrodes that have a stimulus effect, for example stimulation electrodes for heart pacemakers; as used herein the term sensor means an electrode with which measurements are made, for example an electrode for the detection of glucose.

Vitreous carbon electrodes are generally manufactured by producing an electrode blank composed of cross-linked artificial resin from a resin pre-condensate by curing, and this electrode blank is converted into the actual electrode by pyrolysis. Vitreous carbon is formed from the cross-linked artificial resin during the pyrolysis that generally ensues at a temperature between 700 and 2000°C —in an inert atmosphere (see, for example, European Pat. 0 140 127). Electrode blanks can be brought into the desired shape relatively easily by mechanical processing; electrical contacting of vitreous carbon electrodes, however, is difficult.

Making an electrical contact for an implantable vitreous carbon electrode for attachment to a conductor, the vitreous carbon electrode having an electrode head and an electrode shaft, is generally accomplished by plugging or pressing a platinum sleeve onto the electrode shaft. Such a contact, however, is not only complicated to manufacture but also cannot be highly mechanically loaded. The diameter of the electrode shaft is limited due to design features of actuators or sensors, for example the need to mate with a hose-like insulating sleeve or jacket. Given an electrode diameter of 2.37 ram, for example, the diameter of the electrode shaft amounts to 1.34 mm for a heart pacemaker electrode and amounts to 1 mm for a measuring electrode of a catheter-like glucose sensor. Due to the mechanical properties of vitreous carbon, i.e. its brittleness, its Icad-withstanding capability with respect to tension and shearing is therefore extremely low given a contact of this type. For example, the tensile Icadability of the vitreous carbon electrode of a glucose sensor of the above-recited type only amounts to 280 p; with higher loading, the electrode shaft breaks. Such a contact can thus be easily destroyed by a shear fracture of the vitreous carbon during the manipulation of the electrodes, for example during assembly of the sensor. Moreover, further miniaturization of the sensor, which is usually desirable, cannot be achieved because the contact would then be even more sensitive.

SUMMARY OF THE INVENTION

An object of the present invention is to provide a method that allows a simple and mechanically stable electrical contacting of a vitreous carbon electrode to a conductor, particularly in catheter-like actuators and sensors.

The above object is inventively achieved in a method wherein an electrode blank of a cross-linked artificial resin is provided with a bore that partially longitudinally penetrates the electrode body, a solid or hollow pin composed of a biocompatible, refractory metal is introduced into the bore, the pin having smaller dimensions than the bore and projecting from the electrode body, and the electrode blank is subjected to a pyrolysis, whereby the cross-linked artificial resin is converted into vitreous carbon and the electrode body shrinks onto the pin.

In another embodiment of the inventive method, an electrode blank of a crosslinked artificial resin is provided with a bore that completely longitudinally penetrates the electrode body, a sleeve composed of a biocompatible, refractory metal is introduced into the bore, the outside diameter of the sleeve being smaller than the diameter of the bore and the sleeve projecting from the electrode body at both sides, and the electrode blank is subjected to a pyrolysis, whereby the cross-linked artificial resin is converted into vitreous carbon and the electrode body shrinks onto the sleeve.

DESCRIPTION OF THE PREFERRED EMBODIMENTS

In each of the embodiments of the method set forth above, a shrinkage that can amount to up to about 25% ensues in the pyrolysis of the cross-linked artificial resin during which vitreous carbon arises from the artificial resin. The dimensions of the pin or of the sleeve are therefore selected such that the electrode body shrinks onto the pin or sleeve during the pyrolysis. Expressed in other terms, the inside dimension of the bore (without the pin or sleeve) after the pyrolysis, i.e., after the shrink process, is smaller than the outside dimension of the pin or sleeve. An excellent union between electrode body and pin or sleeve is achieved in this way.

It has proven advantageous for the diameter of the pin in the region located in the bore, or the outside diameter of the sleeve, to be approximately 5 through 15% smaller than the diameter of the bore. Preferably, the dimensions of pin or sleeve are about 10% smaller than the inside dimension of the bore.

A bending stress is absorbed by the metal in the contact produced by the method of the invention, whereby the "weak point" of the electrode shaft is eliminated. The bending stress is then either elastically intercepted or it leads to a deformation without fracture. With regard to the mechanical tensile stress, loads of more than 2 kp can be withstood given an outside diameter of 2.3 mm of the electrode. It is also an advantage, in addition to the much higher loadability of the contact, that the conventional method step of contacting after the pyrolysis is eliminated. This results in a more simplified manufacturing procedure, as well as protecting the electrode surface because it no longer has to be touched after the pyrolysis — and possibly following activation. Further, significantly smaller electrodes can be provided with a contact with the method of the invention than was possible using conventional methods.

It is advantageous given the contact produced with a pin to employ a pin which expands cortically outwardly in the region situated in the bore, i.e., it expands into the electrode body. Alternatively, the bore can be produced so that it expands conically from a smallest diameter at its outer opening to a largest diameter at its interior termination. The Icadability can be increased even more in this way. It is also advantageous to employ a pin which, in its region projecting out of the electrode body, has a larger cross section than in its region located in the bore. This facilitates the application of a hose-like insulation.

In the contacting method of the invention, the pin or sleeve is advantageously composed of a metal having a melting point ≦1500°C. The following metals (and the melting point of each) are preferably employed: titanium (1727°C), platinum (1772° C), tantalum (3030°C) and tungsten (3380°C). The pin or sleeve can alternatively be composed of a platinum/iridium alloy.

The pyrolysis of the cross-linked artificial resin preferably ensues at a temperature ≦1000°C, in an inert atmosphere; nitrogen or argon, for example, can serve as the protective atmosphere. Standard resin pre-condensates, especially resins of precondensed furfuryl alcohol, can serve as initial materials for producing the vitreous carbon, however, precondensates of phenol formaldehyde and furane resins can, for example, also be utilized. These resin pre-condensates are then cross-linked (hardened).

The inventive method shall be set forth in further detail with reference to an exemplary embodiment.

A cylindrical electrode head rounded at one end and composed of a cross-linked artificial resin has a diameter of, for example, 2.94 mm and a height of 3.33 mm and has a central bore with a diameter of 0.99 mm and a length of 2.17 mm. A cylindrical pin of platinum serves for contacting, having a length of 5.0 mm and a diameter of 1.5 mm in the region outside the bore and a length of 1.65 mm and a diameter steadily expanding from 0.86 mm to 0.89 mm in the region inside the bore. The diameter of the pin at the pin end inside the bore (0.89 mm) is thus about 10% smaller than the diameter of the bore (0.99 mm).

When the electrode blank, i.e. the above-described electrode head, is subjected to a pyrolysis at a temperature of about 1100°C, the electrode head shrinks onto the platinum pin, whereby a firm union arises, i.e. a durable and stable contacting.

Although modifications and changes may be suggested by those skilled in the art, it is the intention of the inventor to embody within the patent warranted hereon all changes and modifications as reasonably and properly come within the scope of his contribution to the art.

I claim:

1. A method for producing an electrical contact for a vitreous carbon electrode comprising the steps of:

producing an electrode blank of a cross-linked artificial resin, said resin having a pyrolyzing temperature associated therewith at which said resin becomes pyrolyzed;

producing a longitudinally extending bore terminating inside said electrode blank, said bore having an inner dimension;

providing a pin composed of biocompatible metal having a melting point higher than said pyrolyzing temperature, and having an outer dimension small than said inner dimension of said bore;

inrdoucing said pin into said bore with a portion of said pin projecting from one side of said electrode blank; and pyrolyzing said electrode blank with said pin introduced therein at said pyrolying temperature and thereby cross-linking said artificial resin to convert said artificial resin into vitreous carbon and to shrink said electrode blank onto said pin.

2. A method as claimed in claim 1 wherein said pin has a portion introducible into said bore, and comprising the additional step of conically outwardly tapering said outer dimension of said portion of said pin which is introducible into said bore.

3. A method as claimed in claim 1 wherein the step of producing said bore comprises producing a bore having a conically tapering inner dimension increasing from a smallest dimension at an outer opening of said bore to a largest diameter at an interior termination of said bore.

4. A method as claimed in claim 1 wherein the step of providing a pin comprises a pin having a cross section in said region projection from said electrode blank which is larger than a cross section of a remainder of said pin.

5. A method as claimed in claim 1 wherein said pin has a region introducible into said bore, and wherein the step of providing a pin comprises providing a pin having an outer dimension in said region introducible into said bore which is in a range of from 5% through 15% smaller than said inner dimension of said bore.

6. A method as claimed in claim 1 wherein the step of providing a pin comprises providing a pin composed of biocompatible refractory metal having a melting point greater than or equal to 1500° C.

7. A method as claimed in claim 1 wherein the step of providing a pin comprises providing a pin composed of biocompatible, refractory metal selected from the group consisting of titanium, tantalum, tungsten, platinum and platinum/iridium alloys.

8. A method as claimed in claim 1 wherein the step of pyrolizing said electrode blank with said pin introduced therein comprises pyrolizing said electrode blank with said pin introduced therein at a temperature greater than or equal to 1000° C.

9. A method as claimed in claim 1 wherein the step of providing an electrode blank comprises providing an electrode blank of a cross-linked artificial resin composed of a pre-condensed and cross-linked artificial furfuryl alcohol.

10. A method of producing an electrical contact for a vitresous carbon electrode comprising the steps of:

producing an electrode blank of a cross-linked artificial resin, said resin having a pyrolyzing temperature associated therewith at which said resin becomes pyrolyzed;

producing a longitudinally extending bore terminating blank, said bore having an inner dimension;

providing a pin composed of biocompatiblep metal having a melting point higher than said pyrolyzing temperature, and having an outer outer dimension smaller than said inner dimension of said bore;

introducing said sleeve into said bore with respective portions of said sleeve projecting from opposite sides of said electrode blank; and pyrolyzing said electrode blank with said sleeve introduced therein at said pyrolying temperature and thereby cross-linking said artificial resin to convert said artificial resin into vitreous carbon and to shrink said electrode blank onto said sleeve.

11. A method as claimed in claim 10 wherein said sleeve has a region introducible into said bore, and wherein the step of providing a sleeve comprises providing a sleeve having an outer dimension in said region introducible into said bore which is in a range of from 5% through 15% smaller than said inner dimension of said bore.

12. A method as claimed in claim 10 wherein the step of providing a sleeve comprises providing a sleeve composed of biocompatible, refractory metal having a melting point greater than or equal to 1500° C.

13. A method as claimed in claim 10 wherein the step of providing a sleeve comprises providing a sleeve composed of biocompatible, refractory metal selected from the group consisting of titanium, tantalum, tungsten, platinum and platinum/iridium alloys.

14. A method as claimed in claim 10 wherein the step of pyrolizing said electrode blank with said sleeve introduced therein comprises pyrolizing said electrode blank with said sleeve introduced therein at a temperature greater than or equal to 1000° C.

15. A method as claimed in claim 10 wherein the step of providing an electrode blank comprises providing an electrode blank of a cross-linked artificial resin composed of a pre-condensed and cross-linked artificial furfuryl alcohol.

* * * * *